United States Patent [19]
Hilborn et al.

[11] Patent Number: 6,025,517
[45] Date of Patent: Feb. 15, 2000

[54] FLUOXETINE PROCESS FROM BENZOYLACETONITRILE

[75] Inventors: James Wallace Hilborn, Windsor; Alex Roger Jurgens, Falmouth, both of Canada

[73] Assignee: Sepracor Inc., Marlborough, Mass.

[21] Appl. No.: 09/128,319

[22] Filed: Aug. 3, 1998

[51] Int. Cl.$^7$ ........................ C07C 261/00; C07C 213/00
[52] U.S. Cl. .............................. 560/27; 564/351; 564/348
[58] Field of Search ............................... 560/27; 564/351, 564/348

[56] References Cited

U.S. PATENT DOCUMENTS

| | | | |
|---|---|---|---|
| 4,018,895 | 4/1977 | Molloy et al. | 424/330 |
| 4,194,009 | 3/1980 | Molloy et al. | 424/330 |
| 4,314,081 | 2/1982 | Molloy et al. | 564/347 |
| 4,626,549 | 12/1986 | Molloy et al. | 514/651 |
| 4,868,344 | 9/1989 | Brown | 568/812 |
| 5,104,899 | 4/1992 | Young et al. | 514/646 |
| 5,589,511 | 12/1996 | Young et al. | 514/646 |
| 5,648,396 | 7/1997 | Young et al. | 514/651 |

FOREIGN PATENT DOCUMENTS

| | | |
|---|---|---|
| 0336753 | 4/1989 | European Pat. Off. |
| 0369685 | 10/1990 | European Pat. Off. |
| 0369685 | 11/1990 | European Pat. Off. |
| 0457559 | 7/1991 | European Pat. Off. |
| 0529842 | 6/1993 | European Pat. Off. |
| 0380924 | 6/1994 | European Pat. Off. |
| 0617006 | 9/1994 | European Pat. Off. |
| 2060618 | 7/1981 | United Kingdom . |
| WO94/00416 | 5/1994 | WIPO . |

OTHER PUBLICATIONS

Kumar et al. "A New Chemoenzymatic Enantioselective Synthesis of R–(–)–Tomoxetine, (R)–. . . " *Tetrahedron Letters 32*, 1901–1904 (1991).

Ager and Laneman "Reductions of 1,3–dicarbonyl systems with ruthenium–biarylbisphosphine . . . " *Tetrahedron: Asymmetry 8*, 3327–3355 (1997).

Quiros et al. "Enantioselective reduction of β–keto amides by the fungus . . . " *Tetrahedron Asymmetry 8*, 3035–38 (1997).

Mitchell and Koening "Synthesis of R– and S–Fluoxetine, Norfluoxetine and Related . . . " *Synthetic Comm. 25(8)*, 1231–1238 (1995).

*Primary Examiner*—Paul J. Killos
*Attorney, Agent, or Firm*—Heslin & Rothenberg, P.C.

[57] ABSTRACT

A synthesis of fluoxetine is disclosed. The process begins with benzoylacetonitrile, which is reduced, optionally in the presence of a chiral ligand, to produce the corresponding aminoalcohol, and the amine is carbamoylated without isolation. The alcohol is deprotonated and reacted with 4-chloro- or 4-fluoro benzotrifluoride or with 4-trifluoromethylphenol to provide a carbamate of fluoxetine. The carbamate is reduced with a hydride or with borane to provide fluoxetine free base. The process may be employed for the synthesis of individual enantiomers of fluoxetine.

13 Claims, No Drawings

FLUOXETINE PROCESS FROM BENZOYLACETONITRILE

FIELD OF THE INVENTION

This invention relates to a process for preparing fluoxetine, a commercially available pharmaceutical.

BACKGROUND OF THE INVENTION

Fluoxetine is a selective serotonin uptake inhibitor presently available for the treatment of depression under the trade name Prozac™. Its chemical name is given as N-methyl-3-phenyl-3-[(α,α,α-trifluoro-p-tolyl)oxy] propylamine in much of the literature; its name for indexing in Chemical Abstracts is (+/−)-N-methyl-γ-[4-(trifluoromethyl)phenoxy]benzenepropanamine. Fluoxetine is currently available for therapy as a racemic mixture only. Early reports indicated that there was no advantage to the use of the either pure enantiomer [Robertson et al. *J. Med. Chem.* 31 1412–1417 (1988)] of fluoxetine. However, subsequent publications have suggested advantages to the use of the pure S(+) isomer [U.S. Pat. Nos. 5,104,899 and 5,589,511] and the pure R(−) isomer [U.S. Pat. No. 5,648,396]. Thus, processes for the commercial preparation of racemic fluoxetine and of each of its enantiomers are of considerable value.

Numerous processes are known in the literature. The original U.S. patents to fluoxetine [U.S. Pat. Nos. 4,314,081 and 4,194,009] describe syntheses beginning from 3-dimethylaminopropiophenone, which is reduced with diborane, chlorinated with thionyl chloride, condensed with 4-trifluoromethylphenol, and demethylated with cyanogen bromide and potassium hydroxide in ethyleneglycol. This process was somewhat improved by Robertson et al. [*J. Labeled Compound Radiopharm.* 24, 1397–1404 (1987)] by condensing the alcohol with 4-chlorobenzotrifluoride and by replacing cyanogen bromide with phenylchloroformate.

European application 519842 discloses an improved process in which 3-dimethylamino-1-phenyl-1-propanol is reacted with an alkyl chloroformate and hydrolyzed to provide 3-methylamino-1-phenyl-1-propanol, which is then condensed with 4-chloro- or 4-fluorobenzotrifluoride. European application 457559 describes a chiral synthesis of the 3-dimethylamino-1-phenyl-1-propanol that is used as a starting material in the foregoing European application. The chiral synthesis accomplished by reduction of the corresponding ketone with lithium aluminum hydride using (2R, 3S)-(−)4-dimethylamino-1,2,-diphenyl-3-methyl-2-butanol as a chiral ligand. A similar chiral reduction has been described by Sakuraba et al. [*Syn. Lett.* 1991, 689–690] using a different chiral reducing agent. Another approach described in European patent 380924 proceeds by reduction of ethylbenzoylacetate and subsequent aminolysis of the ethyl ester with methylamine. The reduction of ethylbenzoylacetate can also be accomplished in an enantioselective manner using baker's yeast [Kumar et al. *Indian J. Chem.* 31B, 803–809 (1992)]. A ruthenium catalyst having a chiral ligand has been employed in a similar catalytic reduction by Ager and Laneman [*Tet. Asymmetry* 30, 3327–3355 (1997)].

Numerous other methods have been described for preparing single enantiomers of fluoxetine. These include chiral epoxidation of styrene followed by ring opening with acetone cyanohydrin [Mitchell and Koenig *Synthetic Comm.* 25, 1231–1238 (1995)]; asymmetric borane reduction of β-chloropropiophenone [Corey et al. *Tet. Lett.* 30, 5027 (1989)]; and asymmetric epoxidation/reduction [Gao et al. *J. Org. Chem.* 53, 4081–4085 (1988)].

SUMMARY OF THE INVENTION

This invention relates to an improved process for the preparation of fluoxetine, and, in particular, individual fluoxetine enantiomers.

In one aspect, the invention relates to a process for preparing fluoxetine. The process, which is shown in Scheme I, comprises the steps of:

(a) reducing benzoylacetonitrile 1 to provide α-(2-aminoethyl)benzenemethanol 2;

(b) reacting the α-(2-aminoethyl)benzenemethanol with an alkoxycarbonyl acylating agent to form an N-(3-hydroxy-3-phenylpropyl)urethane 3;

(c) reacting the N-(3-hydroxy-3-phenylpropyl)urethane with a 4-(trifluoromethyl)phenyl synthon under arylalkyl ether-forming conditions to provide an N-[3-[4-(trifluoromethyl)phenoxy]-3-phenylpropyl)urethane 4; and (d) reducing the N-[3-[4-(trifluoromethyl)phenoxy]-3-phenylpropyl)urethane to provide N-methyl-3-phenyl-3-[(α,α,α-trifluoro-p-tolyl)oxy]propylamine 5.

The reduction in step (a) and (d) may be accomplished with borane or a metal hydride and, in the case of (a), may be carried out in the presence of a chiral ligand, which will then provide α-(2-aminoethyl)benzenemethanol 2 enriched in a single enantiomer. The acylation, step (b), may be accomplished using a chloroformate or dicarbonate as the alkoxycarbonyl acylating agent.

In step (c), the N-(3-hydroxy-3-phenylpropyl)urethane 3 may be converted to the N-[3-[4-(trifluoromethyl)phenoxy]-3-phenylpropyl)urethane 4 by reacting with a strong base followed by 4-fluoro- or 4-chlorobenzotrifluoride or by reacting 4-(trifluoro methyl) phenol with diethylazodicarboxylate and a trivalent phosphorus compound. If desired, N-methyl-3-phenyl-3-[(α,α,α-trifluoro-p-tolyl)oxy] propylamine 5, also known as fluoxetine free base, may be converted to a salt, such as fluoxetine hydrochloride 6, by treatment of a solution of the free base with a salt-forming acid, such as anhydrous HCl in ether.

The process is particularly useful for the preparation of single enantiomers of fluoxetine, providing S-fluoxetine of useful optical purity (>75% ee) and good chemical yield from benzoylacetonitrile.

SCHEME I

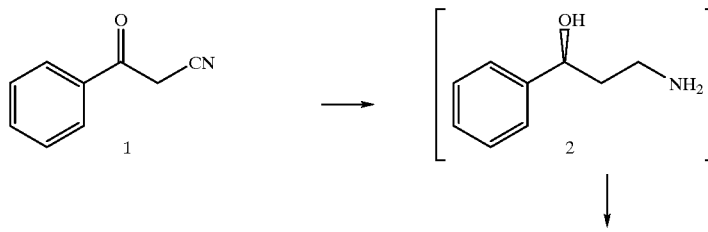

-continued

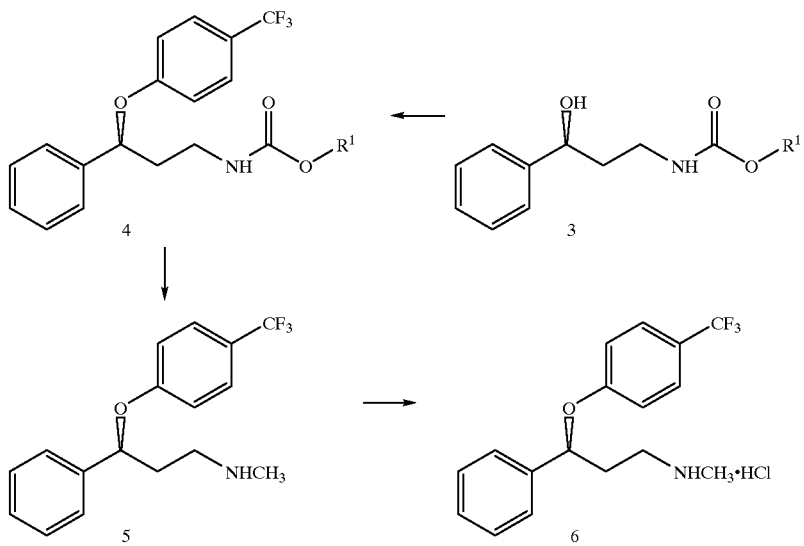

DETAILED DESCRIPTION OF THE INVENTION

The overall synthesis described in Scheme 1 can be further characterized as follows: The process begins with commercially available benzoylacetonitrile 1. The benzoylacetonitrile is reduced, optionally in the presence of a chiral ligand, to produce α-(2-aminoethyl)benzenemethanol 2. Preferred chiral reagents are the borane aminoindanol reagents described by Gao et al. [U.S. Pat. No. 5,495,0541], but other combinations of borane and a chiral ligand are possible, as are other metal hydrides, such as asymmetric alkyl aluminum hydrides. The α-(2-aminoethyl)benzenemethanol 2 is not commonly isolated, but is instead reacted directly to form the urethane 3, wherein $R^1$ is lower alkyl, cycloalkyl, substituted alkyl, arylalkyl, substituted arylalkyl, heteroaryl, heteroarylalkyl or substituted heteroarylalkyl. This transformation is conveniently accomplished with a chloroformate (e.g. ethyl and benzyl chloroformates) or with a dicarbonate (e.g. di-tert-butyldicarbonate). Numerous reagents for the formation of urethanes from amines are described in Greene and Wuts *Protective Groups in Organic Synthesis* Second Edition John Wiley & Sons, New York 1991, pages 315–348, which is incorporated herein by reference. The term "alkoxycarbonyl acylating agent" refers to these reagents having the general formula $R^1OC(O)X$, in which X is a group displaceable by an amine. Throughout this application, various references are referred to within parentheses or square brackets. The disclosures of these publications in their entireties are hereby incorporated by reference into this application.

Several options are available for the arylalkyl ether formation, i.e. conversion of the urethane-alcohol 3 to the N-[3-[4-(trifluoromethyl)phenoxy]-3-phenylpropyl) urethane 4. The alcohol 3 may be deprotonated with a strong base such as sodium hydride in anhydrous solvent such as DMSO and the resulting sodium alcoholate reacted with a 4-chloro- or 4-fluoro- benzotrifluoride. Alternatively, the alcohol 3 may be deprotonated with sodium hydroxide in DMSO and arylated in similar fashion. A third alternative is the reaction of the alcohol 3 with 4-trifluoromethyl phenol under Mitsunobu conditions with trivalent phosphorous and an azodicarboxylate. Triphenylphosphine is a convenient source of trivalent phosphorus; diethyl azodicarboxylate and diisopropyl azodicarboxylate are convenient azodicarboxylates. It is important to note that the first two routes, via the alcoholate anion, result in retention of the configuration of the benzylic carbon, whereas the Mitsunobu reaction preserves optical purity, but with inversion.

The N-[3-[4-(trifluoromethyl)phenoxy]-3-phenylpropyl) urethane 4 is then reduced using a hydride reagent, such as lithium aluminum hydride or sodium bis(2-methoxy-ethoxy) aluminum hydride, or a borane reagent, such as borane dimethyl sulfide. After workup, the free base 5 of fluoxetine is obtained.

Finally, the fluoxetine free base 5 may be converted to fluoxetine hydrochloride 6 by treatment with anhydrous HCl and recrystallization.

The graphic representations of racemic, ambiscalemic and scalemic or enantiomerically pure compounds used herein are taken from Maehr *J. Chem. Ed.* 62, 114–120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. Thus, the formula 6 means either of the pure enantiomers of that pair:

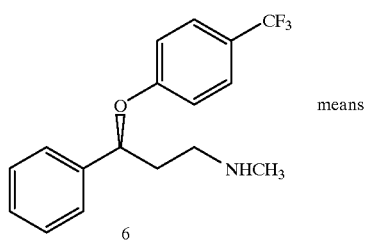

-continued

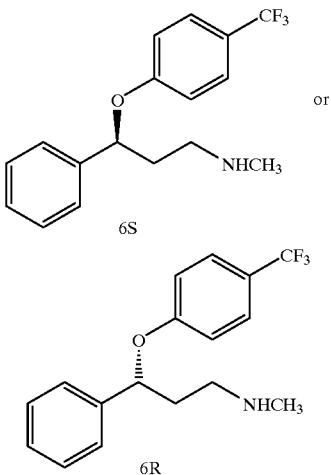

The term "enantiomeric excess" is well known in the art and is defined for a resolution of ab→a+b as $$ee_a = \left(\frac{\text{conc. of } a - \text{conc. of } b}{\text{conc. of } a + \text{conc. of } b}\right) \times 100$$

The term "enantiomeric excess" is related to the older term "optical purity" in that both are measures of the same phenomenon. The value of ee will be a number from 0 to 100, zero being racemic and 100 being pure, single enantiomer. A compound which in the past might have been called 98% optically pure is now more precisely described as 96% ee.; in other words, a 90% e.e. reflects the presence of 95% of one enantiomer and 5% of the other in the material in question.

ABBREVIATIONS AND DEFINITIONS

The following abbreviations and terms have the indicated meanings throughout:
Ac=acetyl
AIBMe=2-methyl4H-tetrahydroindeno[1,2-d][1,3,2]oxazaborole
BNB=4-bromomethyl-3-nitrobenzoic acid
Boc=t-butyloxy carbonyl
Bu=butyl
c-=cyclo
DBU=diazabicyclo[5.4.0]undec-7-ene
DCM=dichloromethane=methylene chloride=CH$_2$Cl$_2$
DEAD=diethyl azodicarboxylate
DIC=diisopropylcarbodiimide
DIEA=N,N-diisopropylethyl amine
DMAP=4-N,N-imethylaminopyridine
DMF=N,N-dimethylformamide
DMSO=dimethyl sulfoxide
DVB=1,4-divinylbenzene
EEDQ=2-ethoxy-1-ethoxycarbonyl-1,2-dihydroquinoline
Fmoc=9-fluorenylmethoxycarbonyl
GC=gas chromatography
HATU=O-(7-Azabenzotriazol-1-yl)-1,1,3,3-tetramethyluronium hexafluorophosphate
HOAc=acetic acid
HOBt=hydroxybenzotriazole
Me=methyl
mesyl=methanesulfonyl
MTBE=methyl t-butyl ether
NMO=N-methylmorpholine oxide
PEG=polyethylene glycol
Ph=phenyl
PhOH=phenol
PfP=pentafluorophenol
PPTS=pyridinium p-toluenesulfonate
PyBroP=bromo-tris-pyrrolidino-phosphonium hexafluorophosphate
rt=room temperature
sat'd=saturated
s-=secondary
t-=tertiary
TBDMS=t-butyldimethylsilyl
TFA=trifluoroacetic acid
THF=tetrahydrofuran
TMOF=trimethyl orthoformate
TMS=trimethylsilyl
tosyl=p-toluenesulfonyl
Trt=triphenylmethyl

EXAMPLES

Preparation of N-Protected AminoAlcohol (3):

To a 500 mL three necked flask was added 5.7 mL of AIBMe catalyst solution (~1M solution, 5.7 mmol, prepared from 8.95 g of (1R,2S)-aminoindanol with 5 g of trimethylboroxine in toluene according to U.S. Pat. No. 5,495,054). To this solution was added 25 mL of dry THF followed by 0.57 mL of borane-dimethylsulfide complex (~10M, 5.7 mmol). This solution was cooled to −15° C. To this solution was added a solution of 5.5 g of benzoylacetonitrile (0.0379 mol) dissolved in 120 mL of dry THF simultaneously with a solution of 2.05 mL of borane-dimethylsulfide complex (~10M, 2.05 mmol) in 7 mL of THF maintaining the reaction temperature below −10° C. After the two solutions were added the reaction was allowed to warm to room temperature overnight. To this solution was then added 2.5 mL of the borane-dimethylsulfide complex (~10 M, 2.5 mmol) and the mixture was heated to reflux. After stirring for an extended period of time the reaction was checked for completion. This solution was quenched by slow addition of a 0.02 M NaOH aqueous solution. To this solution was added a solution of 1.70 g of solid NaOH in 60 mL of water. To this solution was then added 9.1 g (0.0417 mol) of di-t-butyl dicarbonate and the solution was stirred for 4 hours until the reaction was shown to be complete. The material was worked up and purified by column chromatography to yield the N-Boc protected aminoalcohol. Yield 8.39 g; yield 88%.
$^1$H NMR ppm (δ), CDCl$_3$ 7.36 (s, 5H), 4.90–4.80 (s, 1H), 4.75 (t, 1H), 3.50–3.40 (s, 1H), 3.20 (m, 2H), 1.87 (m, 2H), 1.46 (s, 9H); $^{13}$C NMR ppm (δ), CDCl$_3$ 157.1, 144.5, 128.7, 127.6, 125.9, 79.8, 71.9, 39.9, 37.8, 28.6.

The Preparation of Coupled N-Protected Amine (4):

To a 250 mL round bottom flask was added 1.50 g (0.0060 mol) of the N-protected aminoalcohol (3). To this was added 60 mL of dry THF. The solution was stirred until all the material was in solution. To this solution was added 1.56 g of α,α,α-trifluoro-p-cresol (0.0096 mol). To this solution was then added 2.50 g of triphenylphosphine (0.0096 mol). The solution was maintained at 15–20° C. and 1.52 mL of diethyl azodicarboxylate (DEAD) (0.0096 mol) was added and allowed to stir overnight.

The THF was removed under vacuum to yield an oil, which was taken up in hexanes to precipitate the triphenylphosphine oxide. The precipitate was removed by filtration and the resulting solution was concentrated under reduced pressure to yield an oil. The oil was purified by column chromatography to yield the desired product (4). Yield 1.54 g (65%)

¹H NMR ppm (δ), CDCl₃ 7.42 (d, 2H), 7.34–7.25 (s, 5H), 6.88 (d, 2H), 5.22 (dd, 1H), 4.70 (bs, 1H), 3.32 (q, 2H), 2.13 (m, 2H), 3.20 (m, 2H), 1.42 (s, 9H); ¹³C NMR ppm (δ), CDCl₃ 160.3, 156.0, 140.6, 128.9, 128.0, 126.8, 126.7, 125.7, 122.5, 115.8, 78.5, 60.4, 38.8, 37.6, 28.4.

The Preparation of Fluoxetine free amine (5):

To a 25 mL round bottom flask was added 0.21 g (5.3×10⁻⁴ mol) of the coupled N-protected amine 4. This material was dissolved in 10 mL of THF and to this solution was added 0.02 g (5.3×10⁻⁴ mol) of LiAlH₄ and the solution refluxed for 3 hours. The solution was cooled to room temperature and stirred overnight. In the morning a 10% aqueous NaOH solution was added slowly. The layers were separated. The aqueous layer was extracted with EtOAc and organic layers combined, dried (MgSO4) and filtered and rotoevaporated.

The material was used as is for the next step, but it can be purified by column chromatography if needed.

¹H NMR ppm (δ), CDCl₃ 7.42 (d, 2H), 7.32–7.23 (s, 5H), 6.88 (d, 2H), 5.29 (dd, 1H), 4.09 (bs, 1H), 2.78 (t, 2H), 2.44 (s, 3H), 2.25–2.00 (m, 2H); ¹³C NMR ppm (δ), CDCl₃ 160.4, 140.8, 128.9, 127.9, 126.8, 126.7, 125.8, 122.2, 115.8, 78.7, 48.2, 38.4, 36.2.

The Preparation of Fluoxetine Hydrochloride (6): To a 3.0 L round bottom flask was added 25.5 g (0.0824 mol) of fluoxetine free amine 5. To this was added 850 mL of diethyl ether and the amine was dissolved. To this solution was added 150 mL of an ethereal hydrochloric acid solution (0.069 mol HCl/ 100 mL). The reaction was stirred for 30 minutes and then the ether was rotoevaporated to dryness. The solid was taken up in a minimum of ethyl acetate and hexane was added until crystals started forming. The white solid was placed in the refrigerator for 14 hours at ~5° C. The solution was filtered and dried to give 25.75 g of fluoxetine hydrochloride (90%).

¹H NMR ppm (δ), CDCl₃ 7.43–7.23 (m, 9H), 5.71 (s, 2H, NH2), 5.38 (dd, 1H, CH—O), 2.90 (m, 2H), 2.50 (s, 3H, NCH3), 2.35–2.18 (m, 2H). ¹³C NMR ppm (δ), CDCl₃ 160.2, 140.3, 128.9, 128.1, 126.8, 126.7, 125.8, 123.0, 115.8, 78.0, 47.3, 37.0, 35.0.

We claim:

1. A process for preparing fluoxetine comprising the steps of:
   (a) reducing benzoylacetonitrile to provide α-(2-aminoethyl)benzenemethanol;
   (b) reacting said α-(2-aminoethyl)benzenemethanol with an alkoxycarbonyl acylating agent to form an N-(3-hydroxy-3-phenylpropyl)urethane;
   (c) reacting said N-(3-hydroxy-3-phenylpropyl)urethane with a 4-(trifluoromethyl)phenyl synthon under arylalkyl ether-forming conditions to provide an N-[3-[4-(trifluoromethyl)phenoxy]-3-phenylpropyl)urethane; and
   (d) reducing said N-[3-[4-(trifluoromethyl)phenoxy]-3-phenylpropyl)urethane to provide N-methyl-3-phenyl-3-[(α,α,α-trifluoro-p-tolyl)oxy]propylamine.

2. A process according to claim 1 for preparing fluoxetine comprising the steps of:
   (a) reducing benzoylacetonitrile with borane or a metal hydride to provide α-(2-aminoethyl)benzenemethanol;
   (b) reacting said α-(2-aminoethyl)benzenemethanol with a chloroformate or dicarbonate to form an N-(3-hydroxy-3-phenylpropyl)urethane;
   (c) reacting said N-(3-hydroxy-3-phenylpropyl)urethane with 4-(trifluoromethyl)phenol in the presence of a dialkyl azodicarboxylate and a trivalent phosphorus compound to provide an N-[3-[4-(trifluoromethyl) phenoxy]-3-phenylpropyl)urethane; and
   (d) reducing said N-[3-[4-(trifluoromethyl)phenoxy]-3-phenylpropyl)urethane with borane or a metal hydride to provide N-methyl-3-phenyl-3-[(α,α,α-trifluoro-p-tolyl)oxy]propylamine.

3. A process according to claim 1 for preparing fluoxetine comprising the steps of:
   (a) reducing benzoylacetonitrile with borane or a metal hydride to provide α-(2-aminoethyl)benzenemethanol;
   (b) reacting said α-(2-aminoethyl)benzenemethanol with a chloroformate or dicarbonate to form an N-(3-hydroxy-3-phenylpropyl)urethane;
   (c) reacting said N-(3-hydroxy-3-phenylpropyl)urethane with 4-chloro- or 4-fluorobenzotrifluoride in the presence of a strong base to provide an N-[3-[4-(trifluoromethyl)phenoxy]-3-phenylpropyl)urethane; and
   (d) reducing said N-[3-[4-(trifluoromethyl)phenoxy]-3-phenylpropyl)urethane with borane or a metal hydride to provide N-methyl-3-phenyl-3-[(α,α,α-trifluoro-p-tolyl)oxy]propylamine.

4. A process according to claim 1, 2 or 3 wherein said reducing benzoylacetonitrile employs borane or a metal hydride in the presence of a chiral catalyst to provide α-(2-aminoethyl)benzenemethanol enriched in a single enantiomer.

5. A process according to claim 4 wherein said N-methyl-3-phenyl-3-[(α,α,α-trifluoro-p-tolyl)oxy]propylamine is enriched in the (S) enantiomer.

6. A process according to claim 4 wherein said N-methyl-3-phenyl-3-[(α,α,α-trifluoro-p-tolyl)oxy]propylamine is enriched in the (R) enantiomer.

7. A process according to claim 4 wherein said reduction employs borane in the presence of an oxazaborolidine chiral catalyst.

8. A process according to claim 4 wherein said chiral catalyst is a single enantiomer of 1-amino-2-indanol.

9. A process according to claim 2 or 3 wherein, in step (b), said α-(2-aminoethyl)benzenemethanol is reacted with di-t-butyldicarbonate to form t-butyl N-(3-hydroxy-3-phenylpropyl)urethane.

10. A process according to claim 2 or 3 wherein, in step (d), said urethane is reduced with lithium aluminum hydride to provide said N-methyl-3-phenyl-3-[(α,α,α-trifluoro-p-tolyl)oxy]propylamine.

11. A compound of formula

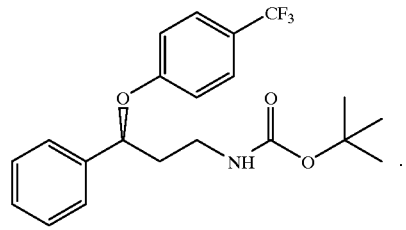

.

12. A compound according to claim 11 of the R configuration.

13. A compound according to claim 11 of the S configuration.

* * * * *